United States Patent
Shaapur et al.

(10) Patent No.: US 8,258,473 B2
(45) Date of Patent: Sep. 4, 2012

(54) METHOD AND APPARATUS FOR RAPID PREPARATION OF MULTIPLE SPECIMENS FOR TRANSMISSION ELECTRON MICROSCOPY

(75) Inventors: Frederick F. Shaapur, Scottsdale, AZ (US); Roger J. Graham, Scottsdale, AZ (US)

(73) Assignee: Nanotem, Inc., Scottsdale, AZ (US)

( * ) Notice: Subject to any disclaimer, the term of this patent is extended or adjusted under 35 U.S.C. 154(b) by 40 days.

(21) Appl. No.: 13/050,561

(22) Filed: Mar. 17, 2011

(65) Prior Publication Data
US 2012/0119084 A1 May 17, 2012

Related U.S. Application Data

(60) Provisional application No. 61/413,083, filed on Nov. 12, 2010.

(51) Int. Cl.
*H01J 37/244* (2006.01)
*H01J 37/20* (2006.01)
(52) U.S. Cl. ............ 250/307; 250/311; 250/440.11; 250/442.11; 250/492.21
(58) Field of Classification Search ............ 250/307, 250/311, 440.11, 442.11
See application file for complete search history.

(56) References Cited

U.S. PATENT DOCUMENTS

| | | | |
|---|---|---|---|
| 6,188,068 B1* | 2/2001 | Shaapur et al. | 850/8 |
| 6,194,720 B1* | 2/2001 | Li et al. | 250/311 |
| 6,420,722 B2* | 7/2002 | Moore et al. | 250/559.27 |
| 6,570,170 B2* | 5/2003 | Moore | 250/492.21 |
| 6,717,156 B2* | 4/2004 | Sugaya et al. | 250/440.11 |
| 6,927,400 B2* | 8/2005 | Rasmussen | 250/442.11 |
| 7,053,383 B2* | 5/2006 | Moore | 250/440.11 |
| 7,112,790 B1* | 9/2006 | Wang | 250/307 |
| 7,205,560 B2* | 4/2007 | Tokuda et al. | 250/492.3 |
| 7,227,140 B2* | 6/2007 | Skidmore et al. | 250/307 |
| 7,297,965 B2* | 11/2007 | Kidron et al. | 250/492.2 |
| 7,315,023 B2* | 1/2008 | Moore | 250/311 |
| 7,375,325 B2* | 5/2008 | Burkhardt et al. | 250/307 |
| 7,408,178 B2* | 8/2008 | Tappel | 250/492.21 |
| 7,511,282 B2* | 3/2009 | Agorio et al. | 250/442.11 |
| 8,168,948 B2* | 5/2012 | Botman et al. | 250/307 |
| 2011/0031397 A1* | 2/2011 | Zaykova-Feldman et al. | 250/307 |
| 2012/0119084 A1* | 5/2012 | Shaapur et al. | 250/307 |

OTHER PUBLICATIONS

Overwijk et al. "Novel Scheme for the Preparation of Transmission Electron Microscopy Specimens with a Focused Ion Beam" J. Vac. Sci. Technol. B, 11(6), Nov./Dec. 1993, pp. 2021-2024.
Shaapur et al. "Evaluation of a new Strategy for Transverse Tern Specimen Preparation by Focused-Ion-Beam Thinning" Mat. Res. Soc. Symp. Proc. vol. 480, pp. 173-180. 1997.
Stevie et al. "Applications of Focused Ion Beams in Microelectronics Production, Design and Development." Surface and Interface Analysis. vol. 23, pp. 61-68. 1995.
Burkhardt et al. "In-Situ Lift-Out of TEM-Lamellae using a Compact and Precise Micromanipulator", NMI 2002.
Lift-Out Shuttle Brochure. Kleindiek Nanotechnik GmbH. 2009.

* cited by examiner

*Primary Examiner* — David A Vanore
(74) *Attorney, Agent, or Firm* — Brown & Michaels, PC

(57) ABSTRACT

A method and apparatus for in-situ lift-out rapid preparation of TEM samples. The invention uses adhesives and/or spring-loaded locking-clips in order to place multiple TEM-ready sample membranes on a single TEM support grid and eliminates the use of standard FIB-assisted metal deposition as a bonding scheme. Therefore, the invention circumvents the problem of sputtering from metal deposition steps and also increases overall productivity by allowing for multiple samples to be produced without opening the FIB/SEM vacuum chamber.

29 Claims, 15 Drawing Sheets

Fig. 2
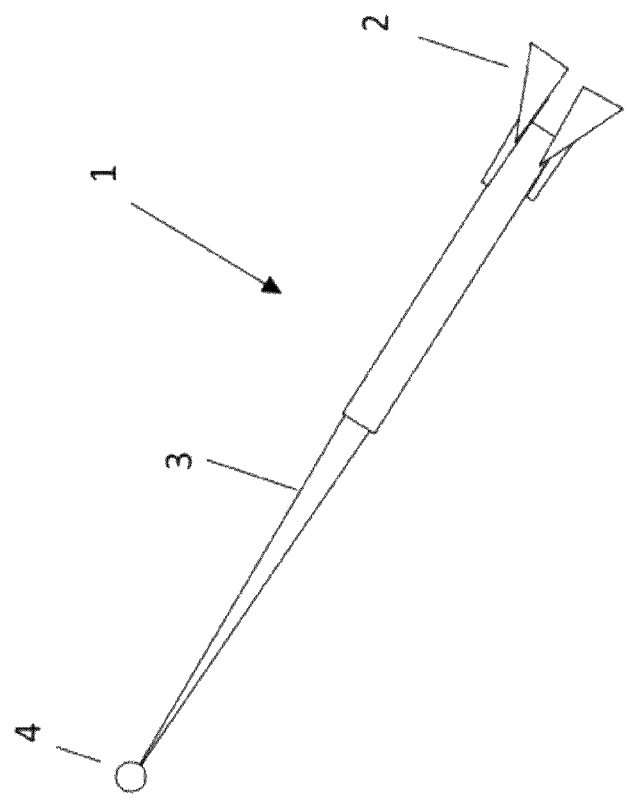
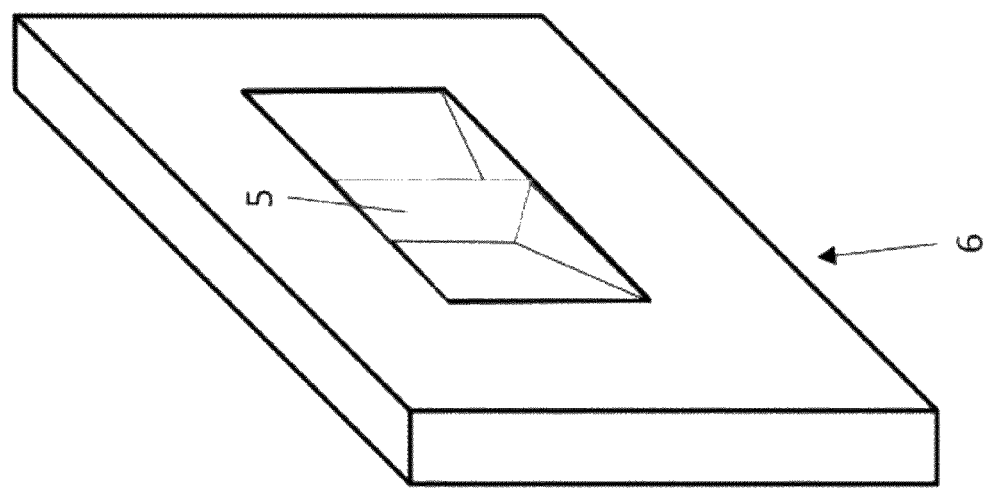

Fig. 4
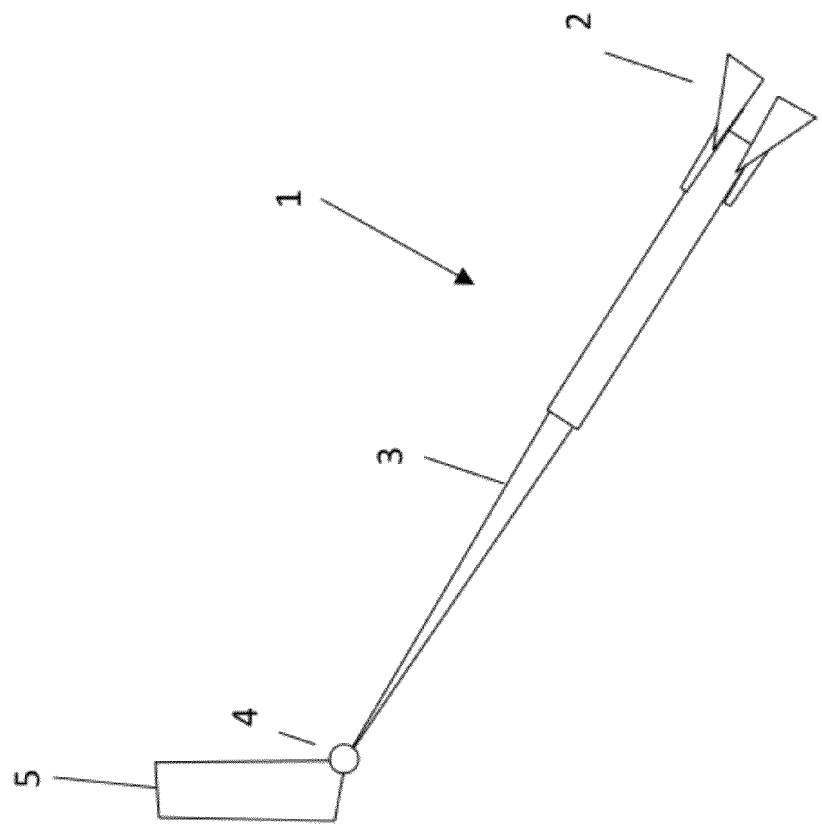
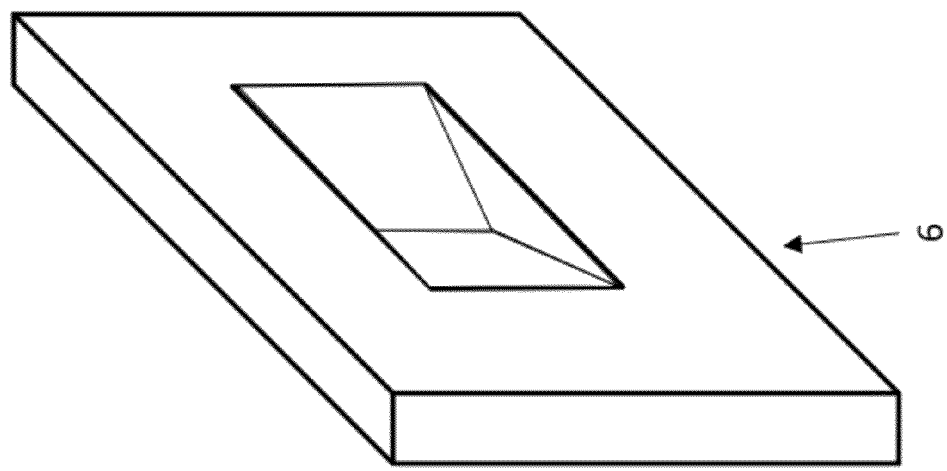

Fig. 5-A
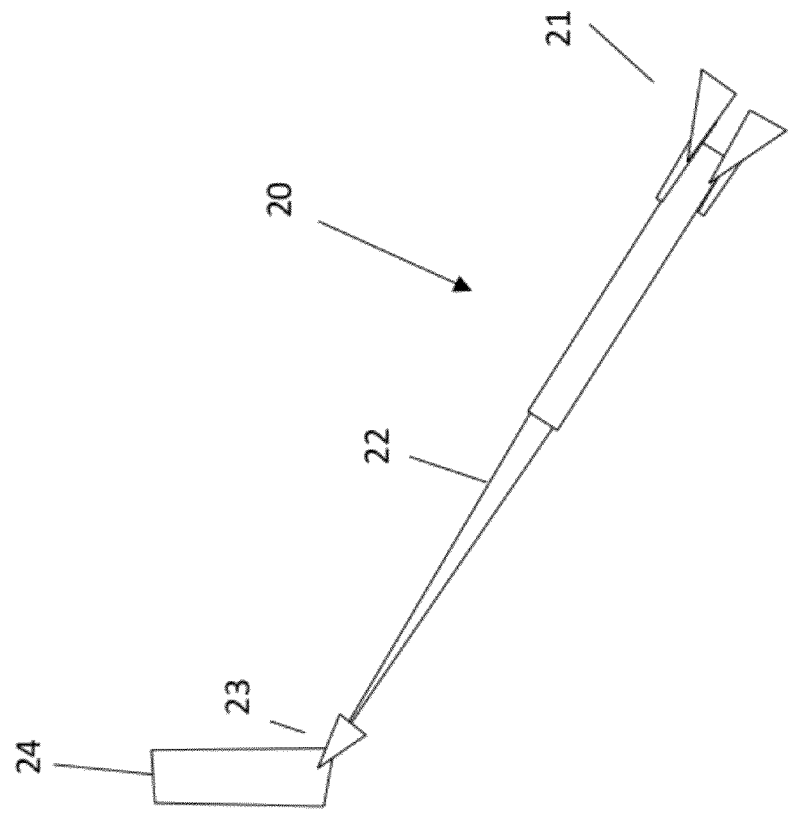
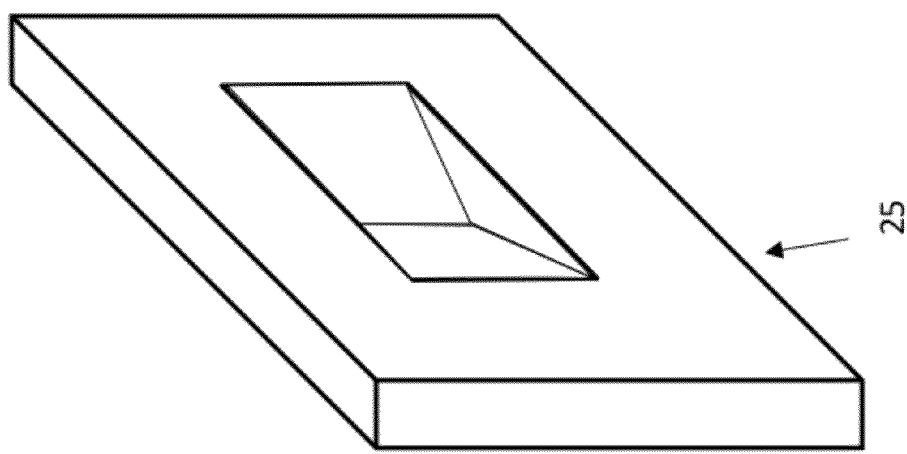

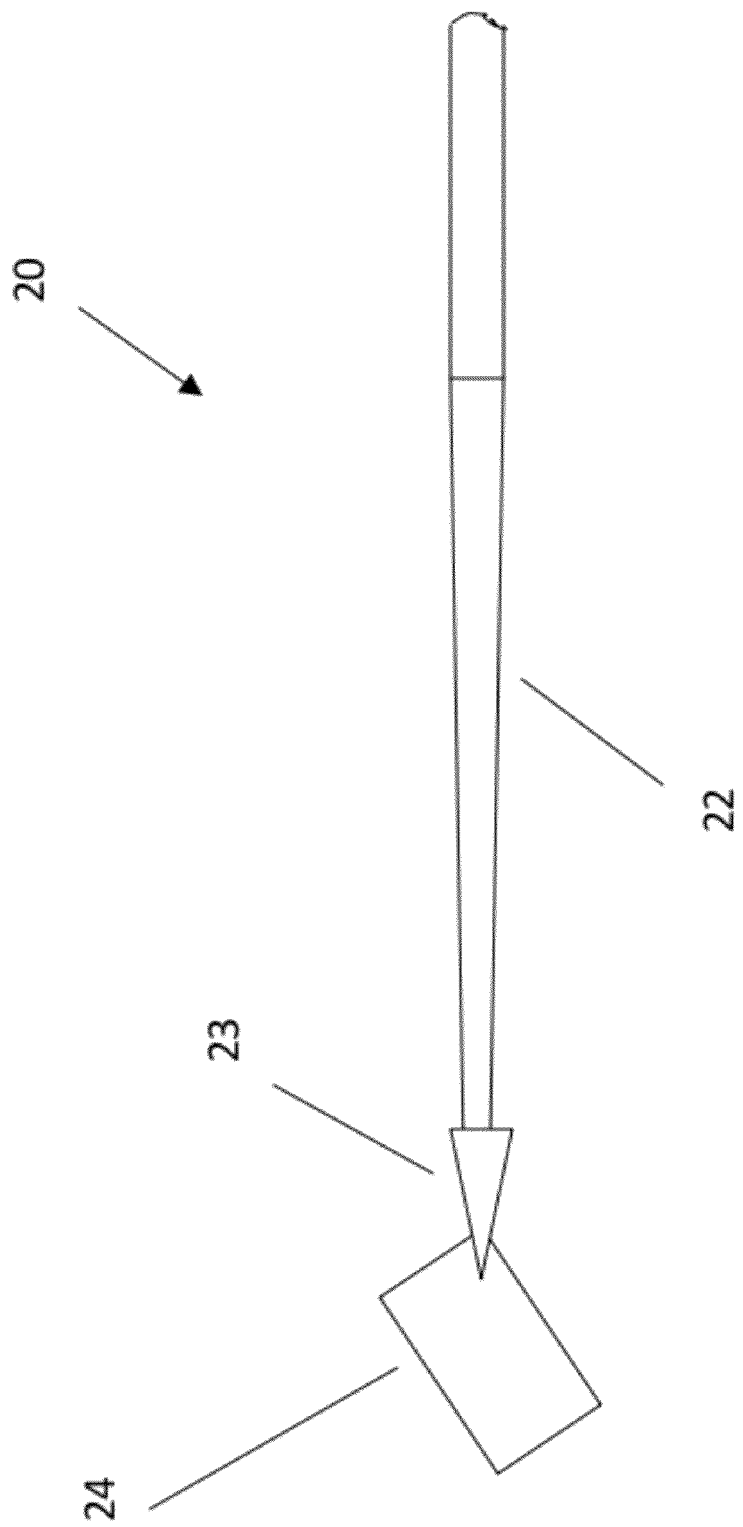
Fig. 5-B

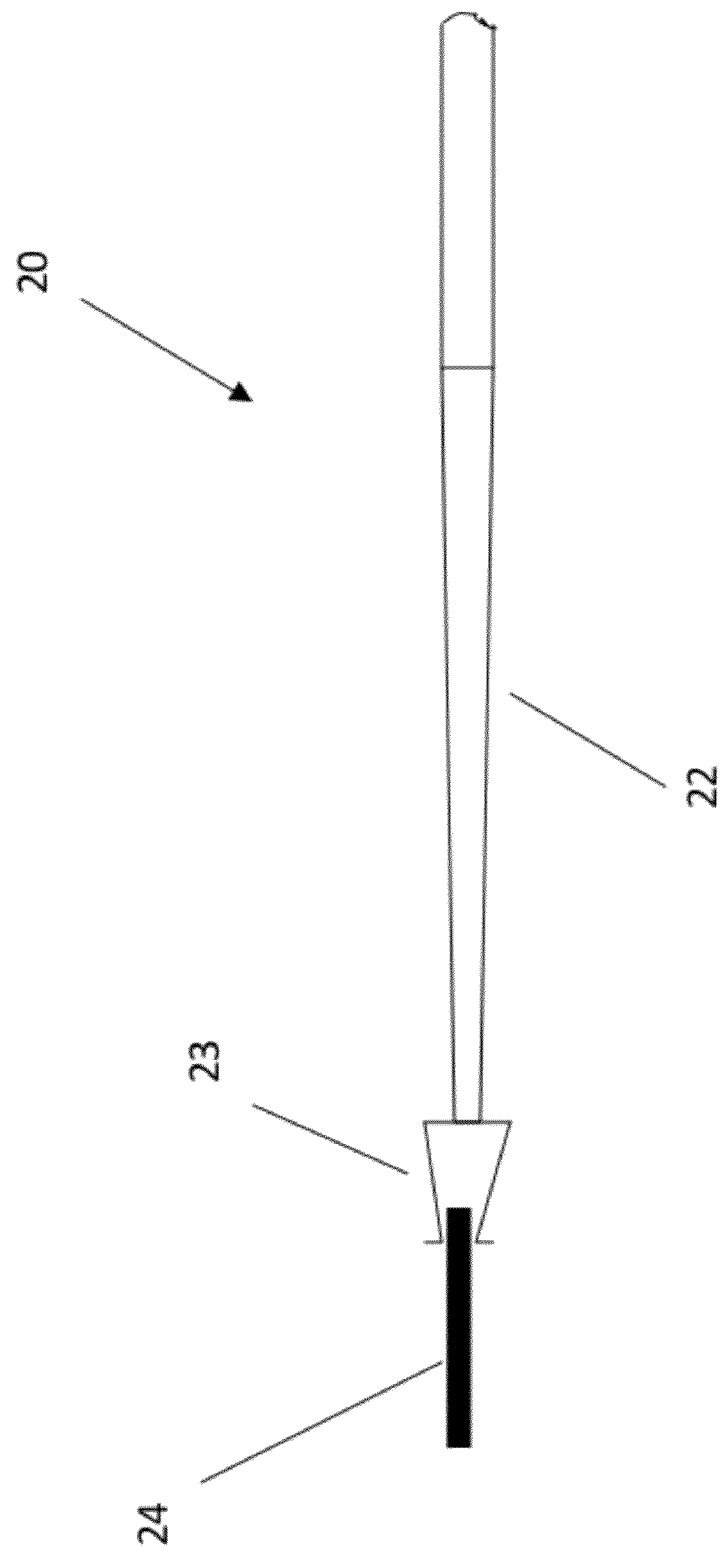
Fig. 5-C

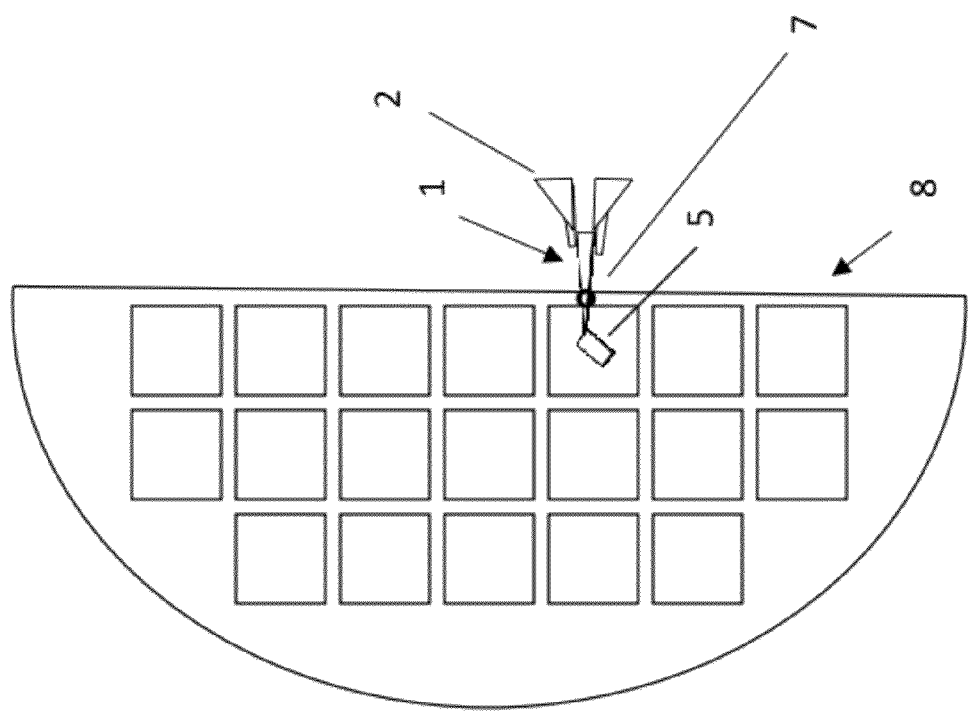

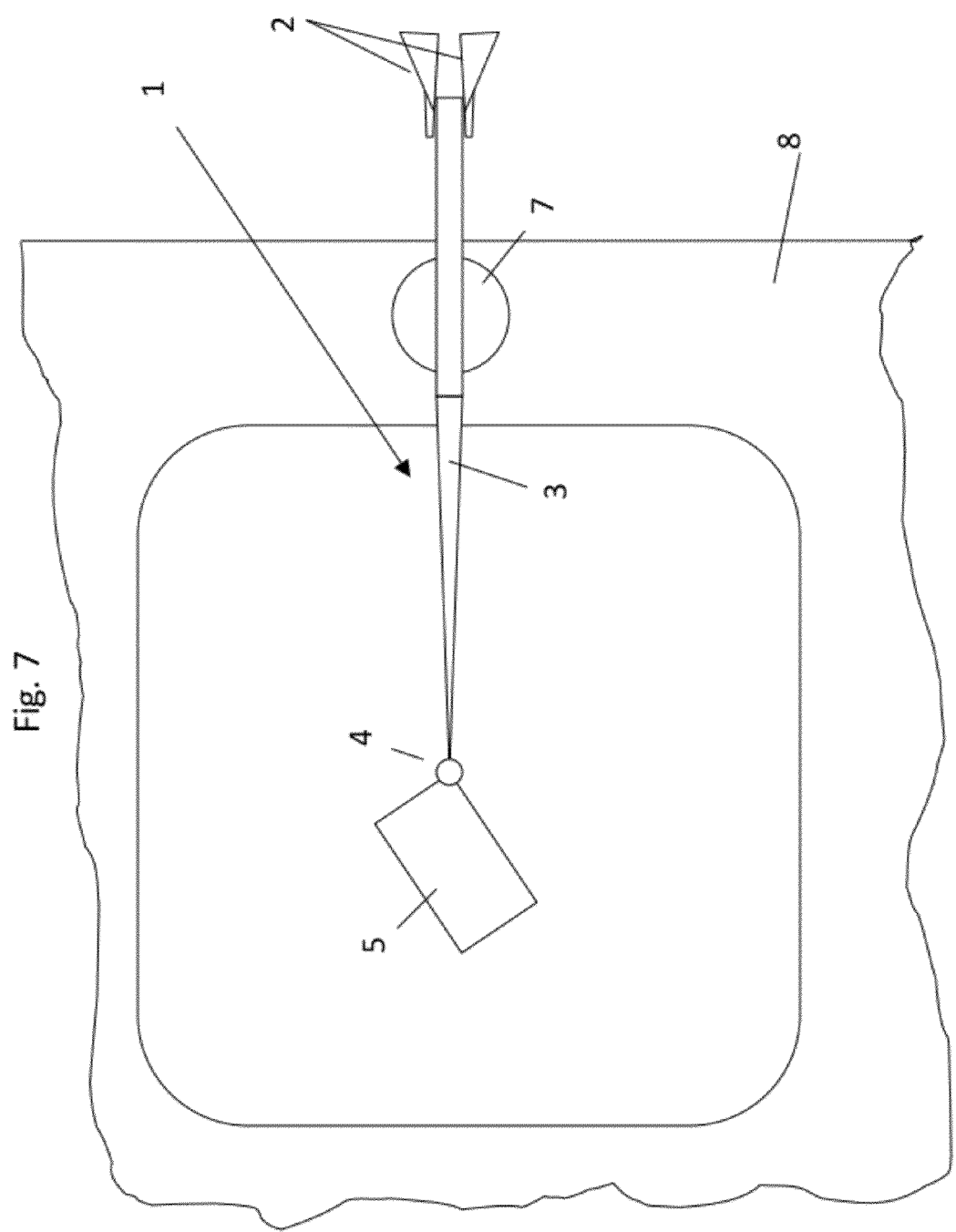

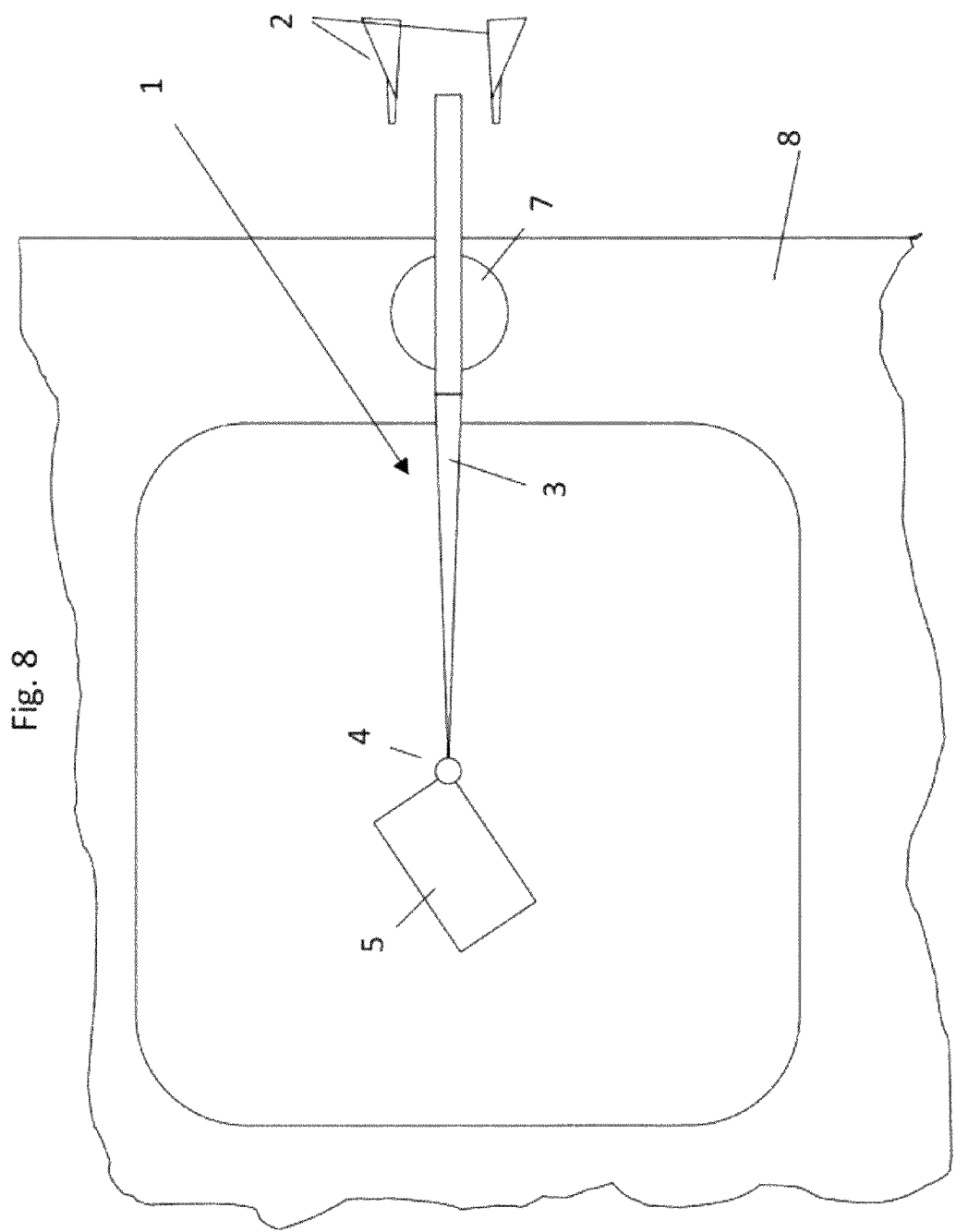

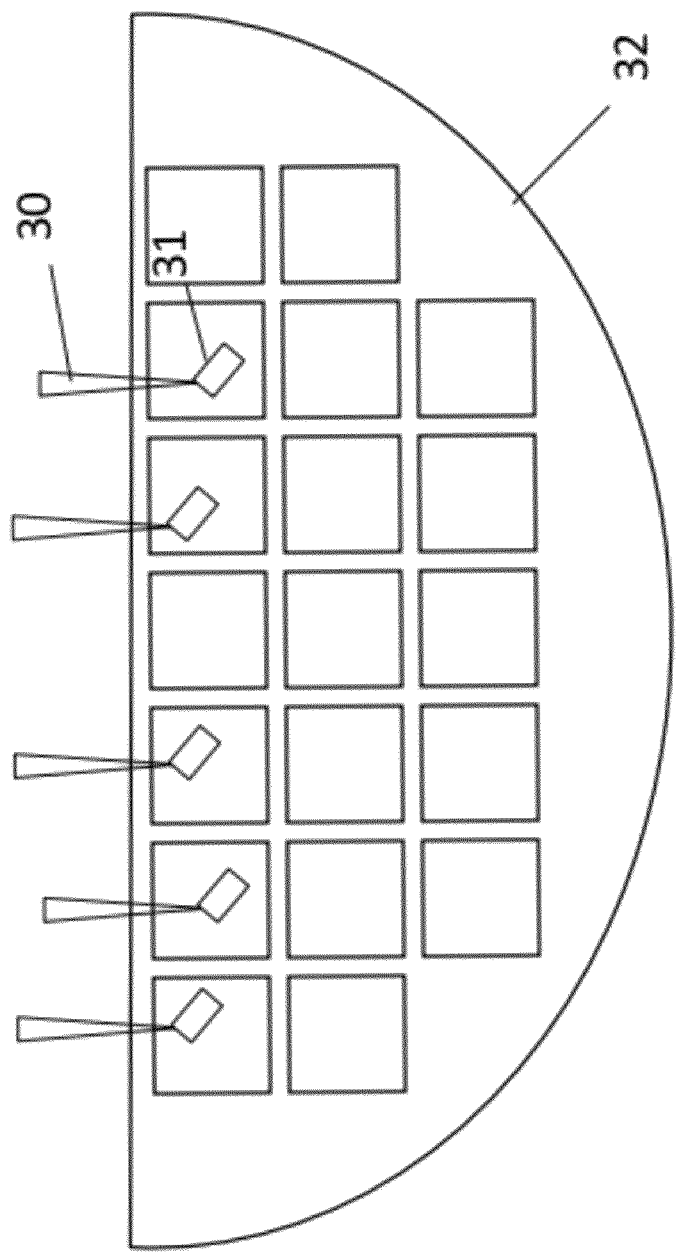

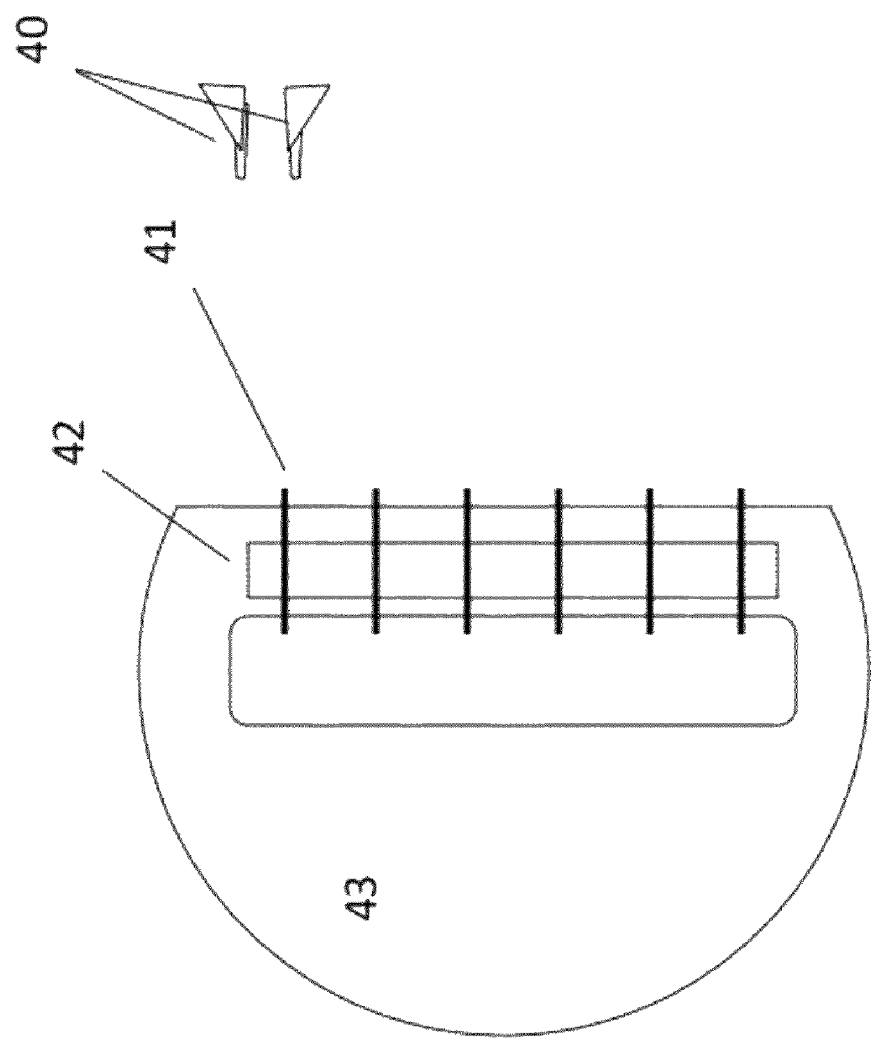
Fig. 9-B

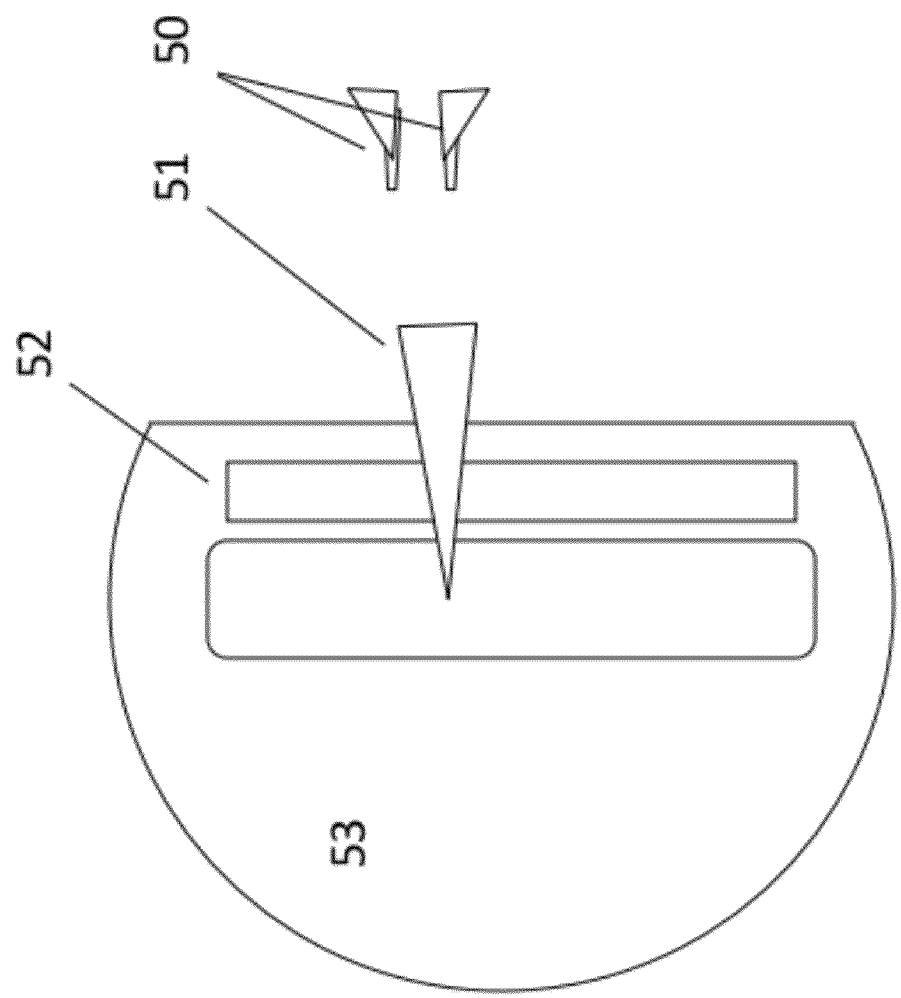
Fig. 9-C

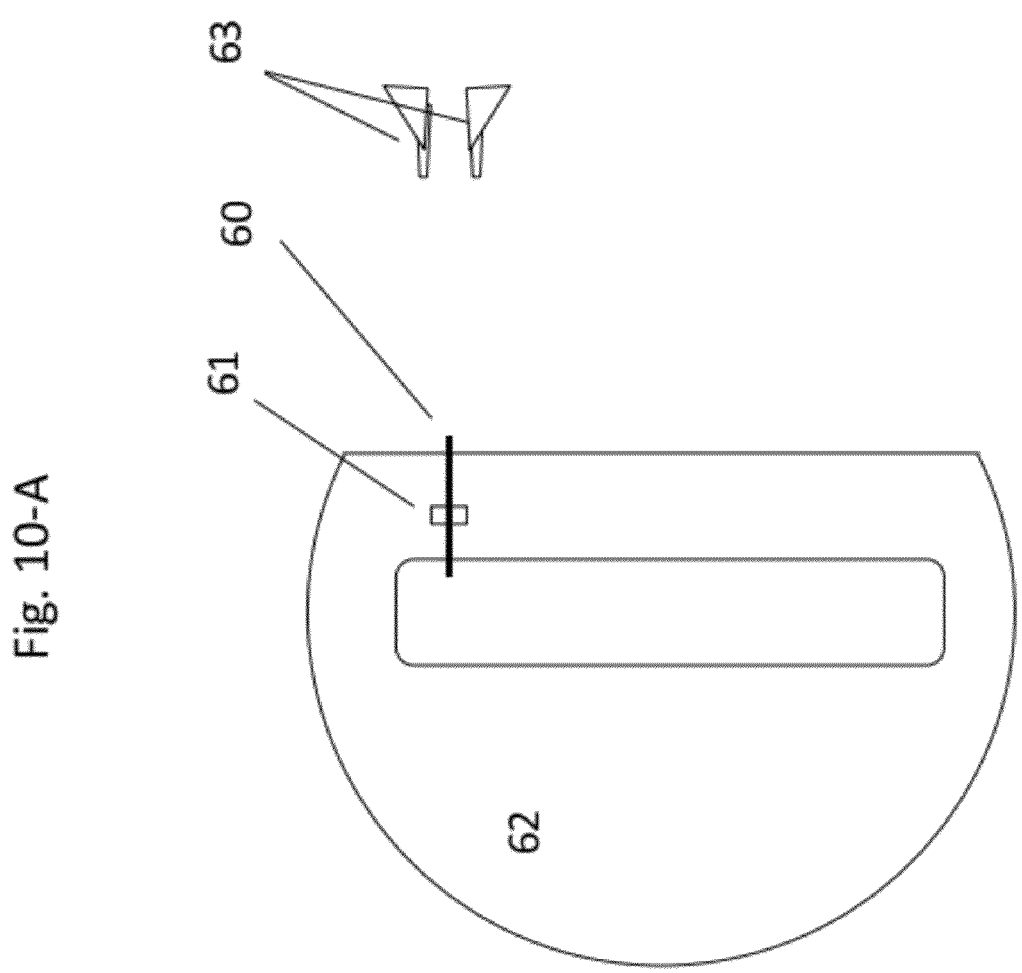

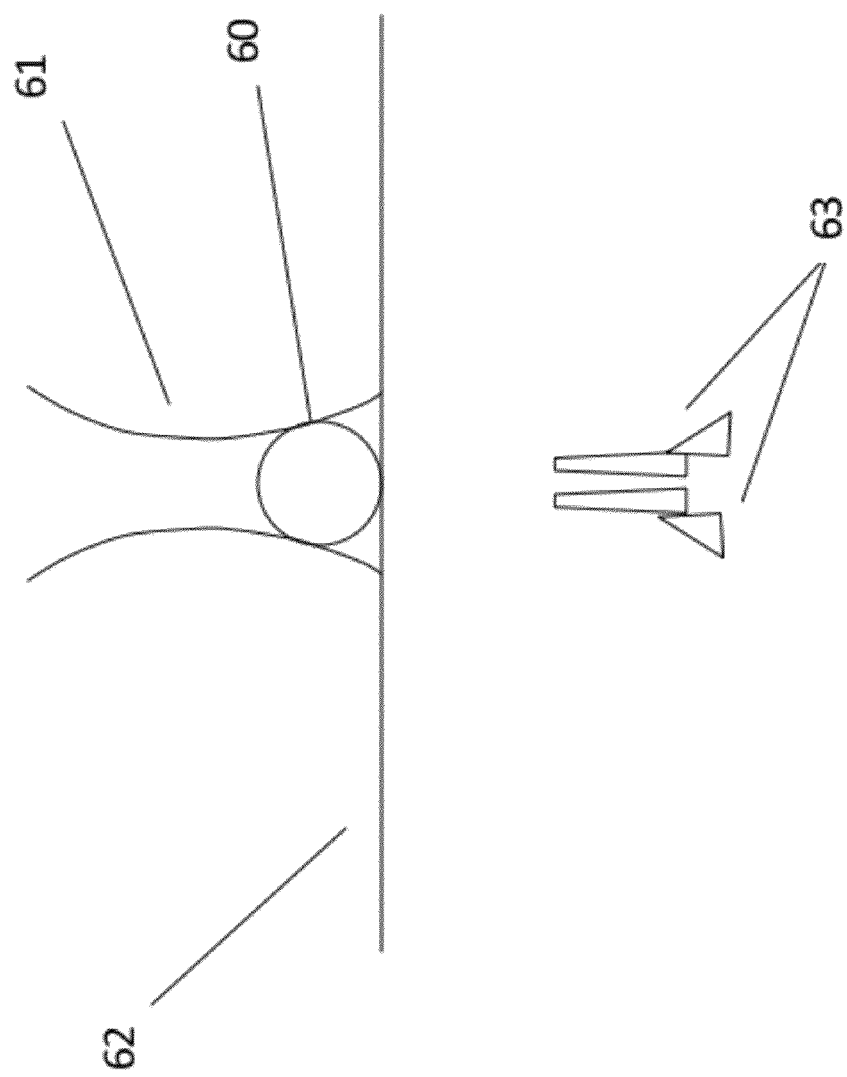
Fig. 10-B

METHOD AND APPARATUS FOR RAPID PREPARATION OF MULTIPLE SPECIMENS FOR TRANSMISSION ELECTRON MICROSCOPY

REFERENCE TO RELATED APPLICATIONS

This application claims one or more inventions which were disclosed in Provisional Application No. 61/413,083, filed Nov. 12, 2010, entitled "METHOD AND APPARATUS FOR RAPID PREPARATION OF MULTIPLE SPECIMENS FOR TRANSMISSION ELECTRON MICROSCOPY". The benefit under 35 USC §119(e) of the United States provisional application is hereby claimed, and the aforementioned application is hereby incorporated herein by reference.

BACKGROUND OF THE INVENTION

1. Field of the Invention

The present invention is in the technical field of methods of sample preparation and manipulation for preparing a specimen for transmission electron microscopy (TEM) examination. More particularly, the present invention is in the technical field of sample preparation and manipulation by methods of in-situ lift-out techniques.

2. Description of Related Art

The standard in-situ lift-out method involves moving a micromanipulator probe to a sample membrane that was previously milled from a wafer by use of a focused ion beam/scanning electron microscope (FIB/SEM) or similar machine. This leaves the sample membrane approximately 1-2 microns thick with varying length and height (typically 5-15 micron length and 5-15 micron height). The micromanipulator probe is then welded to the sample membrane by ion beam assisted metal deposition. When the weld is secured, the sample membrane is then cut from the wafer by a focused ion beam (FIB) and extracted from the wafer.

The probe then moves the sample to a transmission electron microscope (TEM) grid where it is welded to the TEM grid by ion beam assisted metal deposition. When the sample membrane is secured to the TEM grid, the probe is cut from the sample by FIB. The sample membrane is then milled again by FIB until it is thin enough for use in a TEM, typically between 50-200 nanometers thick. The entire method is done within the FIB/SEM machine chamber while it is activated and under vacuum.

The current method of in-situ lift-out has a low productivity, as the number of samples that are produced is relatively low in comparison to the total amount of time and effort that is used for this purpose. Features that shorten the time of preparing a sample and/or increase user productivity are highly desirable in this field.

The current method also has problems in metal deposition steps where excess material may sputter on, and contaminate unintended objects.

SUMMARY OF THE INVENTION

The present invention provides a method and apparatus for in-situ lift-out rapid preparation of samples for electron microscopy. The invention uses adhesives and/or spring-loaded locking-clips in order to place multiple sample membranes on a single support grid and eliminates the use of standard FIB-assisted metal deposition as a bonding scheme. Therefore, the invention circumvents the problem of sputtering from metal deposition steps and also increases overall productivity by allowing for multiple samples to be produced without opening the FIB/SEM vacuum chamber.

BRIEF DESCRIPTION OF THE DRAWING

FIG. 2 is a perspective view of a lift-out system.

FIG. 4 is a perspective view of the continuation of a lift-out system from FIG. 3.

FIG. 5-A is a perspective view of an alternate embodiment of a lift-out system.

FIG. 5-B is a perspective view of an alternate embodiment of a lift-out device.

FIG. 5-C is a side view of an alternate embodiment of a lift-out device of FIG. 5-B.

FIG. 6 is a wide perspective view of a continuation of a lift-out system from FIG. 4.

FIG. 7 is a close up perspective view of FIG. 6 and continuation of a lift-out system from FIG. 6.

FIG. 8 is a close up perspective view of FIG. 6 and continuation of a lift-out system from FIG. 7.

FIG. 9-A is a wide perspective view of a repetition of a lift-out system.

FIG. 9-B is a wide perspective view of an alternate embodiment of FIG. 9-A.

FIG. 9-C is a wide perspective view of an alternate embodiment of FIG. 9-A.

FIG. 10-A is a wide perspective view of an alternate embodiment of FIG. 9-A.

FIG. 10-B is a close up cross sectional view of FIG. 10-A.

DETAILED DESCRIPTION OF THE INVENTION

The Method

Figure 1:
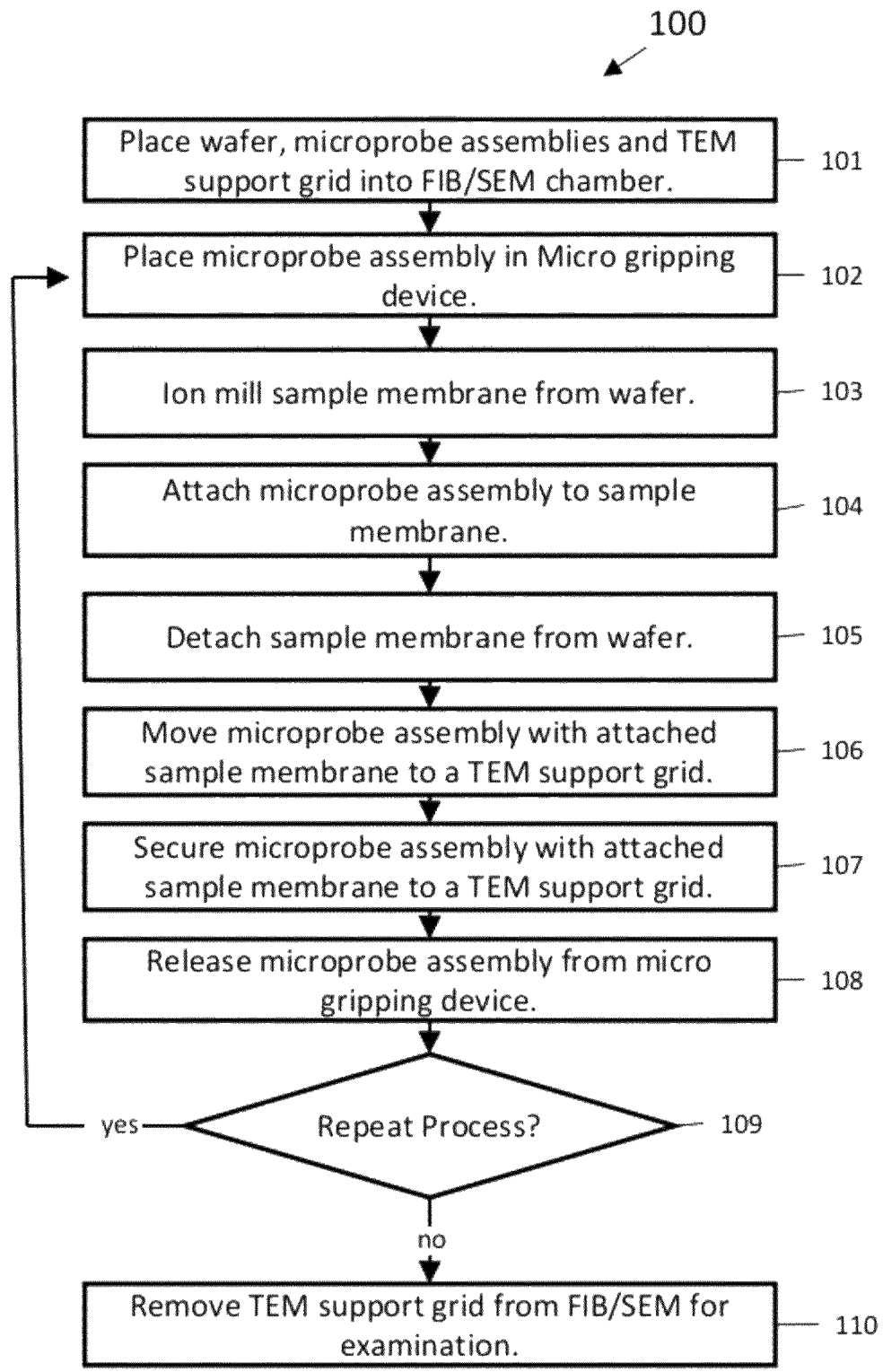
FIG. 1 is a flowchart demonstrating the method.

Referring now to FIG. 1, there is shown a flowchart 100 of the method. The method is comprised of the following steps shown in the flowchart 101: Place wafer, microprobe assemblies and TEM support grid into FIB/SEM chamber—Set up all the necessary parts in order to do an in-situ lift-out according to the method shown in the flowchart 100. A wafer, microprobe assemblies, and TEM support grids are loaded into a FIB/SEM chamber, which is then activated, placing all its contents under vacuum.

102: Place microprobe assembly in micro gripping and manipulation device—a micro gripping and manipulation device reaches and grasps a micromanipulator probe, which has an adhesive or a spring loaded locking clip at the end of it.

103: Ion mill sample membrane from wafer—the FIB/SEM is used to create a sample membrane by etching out portions of the wafer using an ion beam. The sample membrane will be approximately 5-15 microns long, 5-15 microns deep, and less than 200 nanometers thick when the step is completed. The sample membrane will also be partially cut away from the wafer.

104: Attach microprobe assembly to sample membrane—the micro gripping and manipulation device moves the micromanipulator probe so that the adhesive or spring loaded locking clip will touch and attach to the sample membrane. The sample membrane is attached to both the wafer and the microprobe assembly.

105: Detach sample membrane from wafer—the sample membrane is completely severed from the wafer by the FIB/SEM ion beam. The sample membrane is now only attached to the microprobe assembly.

106: Move microprobe assembly with attached sample membrane to a TEM support grid—the microprobe assembly is moved from the wafer to the TEM support grid so that the sample membrane is over a hollow viewing window.

107: Secure microprobe assembly with attached sample membrane to a TEM support grid—the microprobe assembly is attached to the TEM support grid using an adhesive or a spring loaded locking clip so that it is secured to the TEM support grid.

108: Release microprobe assembly from micro gripping and manipulation device—the micro gripping and manipulation device releases the microprobe assembly with sample membrane only attached to the TEM support grid.

109: Repeat Process?—the process may be repeated to create and attach more sample membranes to the TEM support grid.

If yes, return to step 102 and repeat the method;
If no, go on to the last step.

110: Remove TEM support grid from FIB/SEM for examination—the TEM support grid has as many sample membranes attached to it as required by the user and the FIB/SEM is deactivated, releasing the vacuum chamber. The TEM support grid is removed so that it can by viewed by a TEM.

The Apparatus

Figure 3:
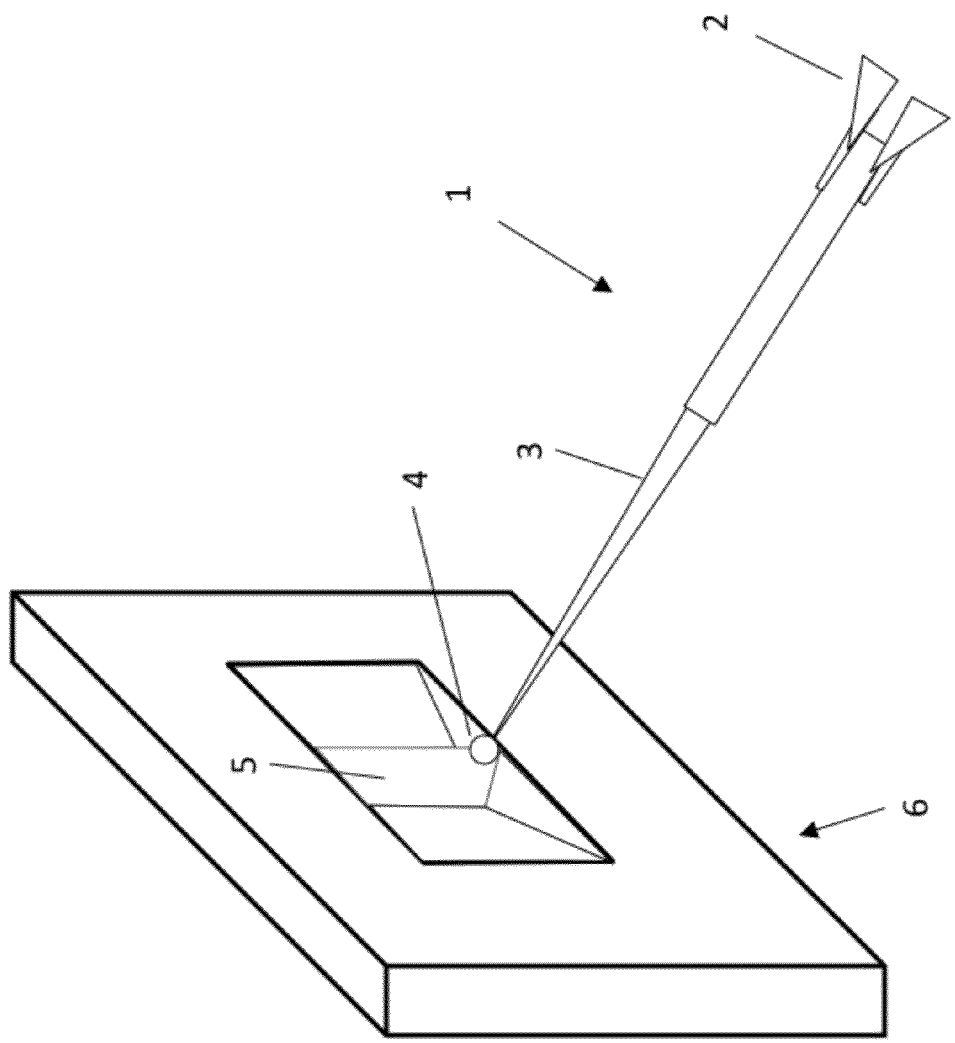
FIG. 3 is a perspective view of the continuation of a lift-out system from FIG. 2.

Referring now to FIG. 2 to FIG. 4, there is shown a microprobe assembly 1 held by a micro gripping and manipulation device 2, which is next to a wafer 6. The microprobe assembly 1 consists of a micromanipulator probe 3 with a sample attachment element—in this embodiment shown as an adhesive 4—at the end opposite the end held by device 2. A sample membrane 5 is part of the wafer 6.

In more detail, still referring to FIG. 2 to FIG. 4, the microprobe assembly 1 is moved by the micro gripping and manipulation device 2 to the sample membrane 5. The sample membrane 5 was previously ion milled by FIB from the wafer 6. The micromanipulator probe 3 is attached to the sample membrane 5 by the adhesive 4. After the adhesive 4 bonds the sample membrane 5 to the micromanipulator probe 3, the sample membrane 5 is detached from the wafer 6 and moved by the micro gripping and manipulation device 2 holding the microprobe assembly 1 with respect to the wafer 6.

In reference to the flowchart 100 shown in FIG. 1, FIG. 2 is shown after the following steps were previously completed; "Place wafer, microprobe assemblies and TEM support grid into FIB/SEM chamber" 101; "Place microprobe assembly in micro gripping and manipulation device" 102; "Ion mill sample membrane from wafer" 103. FIG. 3 is shown after the step, "Attach microprobe assembly to sample membrane" 104. FIG. 4 is shown after the step, "Detach the sample membrane from wafer" 105.

In further detail, still referring to FIG. 2 to FIG. 4, the wafer 6 is loaded into a Focused Ion Beam/Scanning Electron Microscope (FIB/SEM) machine chamber along with the micromanipulator probe 3 and adhesive 4 before beginning the process. The micro gripping and manipulation device 2 is attached to the FIB/SEM machine so that it may manipulate the micromanipulator probe 3. The microprobe assembly 2 must be sufficiently small to capture the sample membrane 5 typically in sizes of five to fifteen microns long, five to fifteen microns deep and approximately 200 nanometers thick or less, but not subject to these limits. The micromanipulator probe 3 may vary in size, length, or geometry, but must be usable with typical manipulating devices that are compatible with FIB/SEM machines. The adhesive 4 may either be preloaded on the micromanipulator probe 3 prior to insertion into a FIB/SEM machine or a small amount of the adhesive may be placed in the FIB/SEM machine where it is accessible to the micromanipulator probe 3.

The construction details of the invention as shown in FIG. 2 to FIG. 4 are that the micromanipulator probe 3 be made of a metal typically used in the art, such as tungsten, molybdenum, or others. The micromanipulator probe 3 is cylindrical and tapers to a point where the adhesive 4 is placed. The adhesive 4, in its preferred embodiment would be usable in vacuum chamber environments of a FIB/SEM machine and would also be curable by exposing it to charged electron particles such as particles exerted from a FIB/SEM machine.

Referring now to FIG. 5-A to FIG. 5-C, there is shown a sample wafer 24 attached to a microprobe assembly 20, which is held by a micro gripping and manipulation device 21, which is near a wafer 25. The microprobe assembly 20 consists of a micromanipulator probe 22 attached to a spring-loaded locking clip 23 at its end.

In more detail, still referring to FIG. 5-A to FIG. 5-C, the microprobe assembly 20 attaches the sample membrane 24 to the micromanipulator probe 22 using the spring loaded locking clip 23. The sample membrane 24 is held in place by the force applied from the spring loaded locking clip 23. The sample membrane 24 was previously ion milled by FIB from the wafer 25. This is an alternate embodiment of the invention.

In further detail, still referring to FIG. 5-A to FIG. 5-C, the wafer 25 is loaded into a Focused Ion Beam/Scanning Electron Microscope (FIB/SEM) machine chamber along with a micromanipulator probe 22 and spring loaded locking clip 23 before beginning the process. The micro gripping and manipulation device 21 is attached to the FIB/SEM machine so that it may manipulate the micromanipulator probe 22. The microprobe assembly 20 must be sufficiently small to capture the sample membrane 24 typically in sizes of five to fifteen microns long, five to fifteen microns deep, and approximately 200 nanometers thick or less, but not subject to these limits.

The micromanipulator probe 22 may vary in size, length, or geometry, but must be usable with typical manipulating devices that are compatible with FIB/SEM machines. The spring loaded locking clip 23 is securely attached to the micromanipulator probe 22 and must apply sufficient force in order to latch and hold onto the sample membrane 24.

The construction details of the invention as shown in FIG. 5-A to FIG. 5-C are that the micromanipulator probe 22 be made of a metal typically used in the art, such as tungsten, molybdenum, or others. The spring loaded locking clip 23 is made of a metal typically used in the art, such that the metal is pliable as to exert a force suitable to hold the sample membrane 24 without inflicting damage to the sample membrane 24. The spring loaded locking clip 23 may vary in shape, size, and geometry as long as it can deliver the same function.

Referring now to FIG. 6 to FIG. 8, there is shown a sample membrane 5 attached to a microprobe assembly 1 held by a micro gripping and manipulation device 2 and attached to a grid adhesive 7 which is attached to a modified TEM mesh support grid 8. The microprobe assembly 1 consists of a micromanipulator probe 3 and an adhesive 4 at the end.

In more detail, still referring to FIG. 6 to FIG. 8, the microprobe assembly 1 with the sample membrane 5 attached by the adhesive 4 is moved by the micro gripping and manipulation device 2 to the modified TEM mesh support grid 8. The microprobe assembly 1 is then bonded by the grid adhesive 7 to the TEM mesh support grid 8 in such a way that the attached sample membrane 5 will be in a hollow viewing window of the modified TEM mesh support grid 8. When the grid adhesive 7 is sufficiently cured so that the microprobe assembly 1 is bonded to the modified TEM mesh support grid 8, the micro gripping and manipulation device 2 releases the microprobe assembly 1. In reference to the flowchart 100 shown in FIG. 1, FIG. 6 and FIG. 7 is shown after the following steps; "Move microprobe assembly with attached sample membrane to a TEM support grid" 106; "Secure microprobe assembly with attached sample membrane to a TEM support grid" 107. FIG. 8 is shown after the step, "Release microprobe assembly from micro gripping and manipulation device" 108.

In further detail, still referring to FIG. 6 to FIG. 8, the modified TEM mesh support grid is placed in a FIB/SEM chamber before beginning the process as shown in the flowchart of FIG. 1. The grid adhesive 7 would be preloaded onto the modified TEM mesh grid 8 or a small amount of the grid adhesive 7 may be placed in the FIB/SEM machine where it is accessible to the microprobe assembly 1. The modified TEM mesh support grid 8 is built with hollow viewing windows where the sample membrane 5 may be viewed later by a TEM or similar machine.

The construction details of the invention as shown in FIG. 6 to FIG. 8 are that the grid adhesive 7 would be curable either inside or outside the vacuum chamber of a FIB/SEM machine. The grid adhesive 7 must also be able to sufficiently secure the microprobe assembly 1 to the modified TEM mesh support grid 8. A modified TEM mesh support grid 8 is a standard 3 millimeter mesh support grid, typically made of metals used in the art, such as copper, molybdenum or others with mesh of viewing windows incorporated into its structure. It would typically be approximately 20-50 microns thick and circular or semicircular with a typical diameter of 3 millimeters. It has been modified by cutting a portion of the mesh support grid off to expose the viewing windows at the edge of the cut.

Referring now to FIG. 9-A, there is shown a modified TEM mesh support grid 32 attached to a group of microprobe assemblies 30 which are each individually attached to a sample membrane 31.

In more detail, still referring to FIG. 9-A, the modified TEM mesh support grid 32 has been processed with multiple sample membranes 31 from their attached microprobes assemblies 30. The method in the flowchart shown in FIG. 1 is repeated until the desired number of sample membranes 31 are placed onto the modified TEM mesh support grid 32. In reference to the flowchart 100 shown in FIG. 1, FIG. 9-A is shown after the following step, "Repeat Process?" 109, has occurred multiple times. The step "Repeat Process?" 109, repeats the method starting at the step, "Place microprobe assembly in micro gripping and manipulation device" 102. When the process no longer needs to be repeated, then the last step, "Remove TEM support grid from FIB/SEM for examination" 110, would follow.

Referring now to the invention shown in FIG. 9-B, there is shown a micro gripping and manipulation device 40 near a group of micromanipulator probes 41 that are attached to a temporary bonding agent 42, which is attached to a modified TEM slotted support grid 43.

In more detail, still referring to FIG. 9-B, the micro gripping and manipulation device 40 may detach the micromanipulator probe 41 and use the previously described method as shown in the flowchart in FIG. 1. After the method described is completed, the micromanipulator probe 41 may be returned to the modified TEM slotted support grid 43. The temporary bonding agent 42 may allow for the micromanipulator probe 41 to detach and reattach to the modified TEM slotted grid 43. This is an alternate embodiment of the invention.

In further detail, still referring to FIG. 9-B, the modified TEM slotted support grid 43 with the temporary bonding agent 42 is placed in a FIB/SEM machine chamber before beginning the process as shown in the flowchart of FIG. 1. The temporary bonding agent 42 allows the micromanipulator probe 41 to bond to the modified TEM slotted grid 43. The micro gripping and manipulation device 40 may grab the micromanipulator probe 41 and pull it from the modified TEM slotted grid 43. The micro gripping and manipulation device 40 may also move a micromanipulator probe 41 to the modified TEM slotted grid 43 where contact with the temporary bonding agent 42 will allow the pieces to bond.

The construction details of the invention as shown in FIG. 9-B are that the temporary bonding agent 42 to be strong enough to securely hold a micromanipulator probe 41 but weak enough to detach the micromanipulator probe 41 from it without damage to the micromanipulator probe 41 when force is applied by the micro gripping and manipulation device 40. The temporary bonding agent 42 may also be able to reattach a micromanipulator probe 41 to the modified TEM slotted support grid 43 by contact and force applied without damage to the micromanipulator probe 41.

The modified TEM slotted support grid 43 is a typical TEM slotted support grid used in the art. It is approximately 3 millimeters in diameter with a slotted hole in the middle. It is made of typical metals used in the art, such as copper, molybdenum or others. The TEM slotted support grid is modified by cutting a portion away from the grid so that the cut is roughly parallel with the long axis of the hollow slot. The extent of cut is variable, but leaves the hollow slot of the slotted TEM grid intact.

Referring now to 9-C, there is shown a micro gripping and manipulation device 50 near a micromanipulator probe 51 which is attached to a temporary bonding agent 52, which is attached to a modified TEM slotted support grid 53.

In more detail, still referring to FIG. 9-C, the micro gripping and manipulation device 50 may manipulate the micromanipulator probe 51 and use the previously described method shown in the flowchart of FIG. 1. After the method described is completed, the micromanipulator probe may be returned to the modified TEM slotted support grid 53. The temporary bonding agent 52 may allow for the micromanipulator probe 51 to detach and reattach to the modified TEM slotted support grid 53. This is an alternate embodiment of the invention.

In further detail, still referring to FIG. 9-C, the modified TEM slotted support grid 53 with the temporary bonding agent 52 is placed in a FIB/SEM machine chamber before beginning the process as shown in the flowchart of FIG. 1. The temporary bonding agent 52 allows a micromanipulator probe 51 to bond to the modified TEM slotted support grid 53. The micro gripping and manipulation device 50 may grab the micromanipulator probe 51 and pull it from the modified TEM slotted support grid 53. The micro gripping and manipulation device 50 may also move a micromanipulator probe 51 to the modified TEM slotted support grid 53 where contact with the temporary bonding agent 52 will allow the pieces to bond.

The construction details of the invention as shown in FIG. 9-C are that the temporary bonding agent 52 be strong enough to securely attach a micromanipulator probe 51 but weak enough to be able to detach the micromanipulator probe 51 from it without damage to micromanipulator probe 51 when force is applied by the micro gripping and manipulation device 50. The temporary bonding agent 52 will also be used to reattach the micromanipulator probe 51 to the modified TEM slotted support grid 53 by contact and force applied without damage to the micromanipulator probe 51. The modified TEM slotted support grid 53 is based on a typical TEM slotted support grid used in the art or a close variation of it. It is approximately 3 millimeters in diameter with a slotted hole in the middle. It is made of typical metals used in the art, such as copper, molybdenum or others. A TEM slotted support grid is modified by cutting a portion away from the grid so that it is roughly parallel with the long axis of the slot. The extent of the cut is variable, but leaves the slotted portion of the grid intact. The micromanipulator probe 51 is flat and made of a metal typically used in the art, such as copper, molybdenum or others.

Referring now to FIGS. 10-A and 10-B, there is shown a micro gripping and manipulation device 63 near a micromanipulator probe 60 which is attached to a spring loaded locking clip 61, which is attached to a modified TEM slotted support grid 62.

In more detail, still referring to FIG. 10-A and FIG. 10-B, the micro gripping and manipulation device 63 may manipulate the micromanipulator probe 60 and use the previously described method shown in the flowchart of FIG. 1. After the method described is completed, the micromanipulator probe 60 may be returned to the modified TEM slotted support grid 62. The spring loaded locking clip 61 may allow for the micromanipulator probe 60 to detach and reattach to the modified TEM slotted support grid 62. This is an alternate embodiment of the invention.

In further detail, still referring to FIG. 10-A and FIG. 10-B, the modified TEM slotted support grid 62 with the spring loaded locking clip 61 is placed in a FIB/SEM machine chamber before the process begins as described in the flowchart of FIG. 1. The spring loaded locking clip 61 allows a micromanipulator probe 60 to attach to the modified TEM slotted support grid 62. The micro gripping and manipulation device 63 may grab the micromanipulator probe 60 and pull it from the modified TEM slotted support grid 62. The micro gripping and manipulation device 63 may also move a micromanipulator probe 60 to the modified TEM slotted support grid 62 where contact and applied force with the spring loaded locking clip 61 will allow the micromanipulator probe 60 to attach to the modified TEM slotted support grid 62.

The construction details of the invention as shown in FIG. 10-A and FIG. 10-B are that the spring loaded locking clip 61 is strong enough to hold a micromanipulator probe 60 but weak enough to be able to detach the micromanipulator probe 60 from it without damage to the micromanipulator probe 60 when force is applied by the micro gripping and manipulation device 63. The spring loaded locking clip 61 must also be able to reattach a micromanipulator probe 60 to a modified TEM slotted support grid 62 by contact and force applied without damage to the micromanipulator probe 60. The spring loaded locking clip 6 may vary in shape, size, and geometry as long as it can deliver the same function.

The modified TEM slotted support grid 62 is a typical TEM support slotted grid used in the art or a close variation of it. It is typically approximately 3 millimeters in diameter with a slotted hole in the middle. It is made of typical metals used in the art, such as copper, molybdenum or others. The modified TEM slotted support grid 62 is modified by cutting a portion away from the grid so that it is roughly parallel with the long axis of the slot. The extent of cut is variable, but leaves the slotted portion of the support grid intact.

The advantages include, without limitation, that it allows for multiple sample membranes to be placed on a single TEM support grid for viewing by a TEM or similar machine. The method further avoids the need for assisted metal weld deposition and its inherent metal sputtering on and around the area of interest for microscopy. The method further allows for SEM only type of machines to continue the lift-out process, thereby freeing the more expensive FIB/SEM machine from the downtime of the in-situ lift-out attachment process.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for in-situ lift-out preparation of samples for electron microscopy in a microscopy chamber having at least one viewing window, using a micro gripping and manipulation device and a microprobe assembly having an adhesive or a spring loaded locking clip at an end, the method comprising:
   a) placing a wafer, microprobe assemblies and a support grid into an electron microscopy chamber;
   b) placing the microscopy chamber under vacuum;
   c) grasping the microprobe assembly with the micro gripping and manipulation device;
   d) creating a sample membrane by etching out portions of the wafer using an ion beam;
   e) using the micro gripping and manipulation device to move the microprobe assembly so that the adhesive or spring loaded locking clip will touch and attach to the sample membrane;
   f) severing the sample membrane from the wafer;
   g) moving the microprobe assembly with the attached sample membrane to the support grid, so that the sample membrane is over a viewing window;
   i) securing the microprobe assembly to the support grid; and
   j) releasing the microprobe assembly from the micro gripping and manipulation device.

2. The method of claim 1, further comprising creating and attaching more sample membranes to the support grid by repeating the method from step c until all sample membranes have been created and attached.

3. The method of claim 1, further comprising the steps of:
   k) deactivating the microscopy chamber, releasing the vacuum; and
   l) removing the support grid.

4. The method of claim 1, wherein the sample membrane is etched in step d to a size in the range of 5-15 microns in length, 5-15 microns in depth and less than 200 nanometers in thickness.

5. The method of claim 1, in which step d further comprises partially cutting the sample membrane away from the wafer.

6. The method of claim 1, in which in the step f the sample membrane is completely severed from the wafer by the FIB/SEM ion beam.

7. The method of claim 1, in which in step i the microprobe assembly is secured to the TEM support grid using an adhesive or a spring loaded locking clip.

8. An apparatus for in-situ lift-out preparation of electron microscopy samples comprising:
 a) a micro gripping and manipulation device;
 b) a microprobe assembly having a first end for gripping by the micro gripping and manipulation device, and a second end; and
 c) an attachment element at the second end of the microprobe assembly.

9. The apparatus of claim 8, in which the attachment element is an adhesive.

10. The apparatus of claim 9, in which the adhesive is usable in a vacuum chamber environment.

11. The apparatus of claim 9, in which the adhesive is curable by exposure to charged electron particles.

12. The apparatus of claim 8, in which the attachment element is a spring loaded locking clip.

13. The apparatus of claim 12, in which the spring loaded locking clip is made of a metal pliable enough to exert a force suitable to hold a sample without inflicting damage to the sample.

14. The apparatus of claim 8, in which the microprobe assembly is made of metal.

15. The apparatus of claim 14, in which the metal is tungsten.

16. The apparatus of claim 14, in which the metal is molybdenum.

17. The apparatus of claim 8, in which the micromanipulator probe is cylindrical and tapers from the first end to a point at the second end.

18. The apparatus of claim 8, further comprising a mesh support grid for supporting a plurality of micromanipulator probes attached to samples.

19. The apparatus of claim 18, in which the mesh support grid further comprises a curable grid adhesive for adhering the micromanipulator probe to the mesh support grid.

20. The apparatus of claim 18, in which the mesh support grid further comprises a slotted support grid.

21. The apparatus of claim 20, in which the slotted support grid has a temporary bonding agent for removably bonding the micromanipulator probe to the slotted support grid.

22. The apparatus of claim 20, in which the micromanipulator probe has a temporary bonding agent for removably bonding the micromanipulator probe to the slotted support grid.

23. The apparatus of claim 18, in which the mesh support grid further comprises a plurality of viewing windows.

24. The apparatus of claim 18, in which the mesh support grid is made of metal.

25. The apparatus of claim 24, in which the metal is copper.

26. The apparatus of claim 24, in which the metal is molybdenum.

27. The apparatus of claim 18, in which the mesh support grid is approximately 20-50 microns thick.

28. The apparatus of claim 18, in which the mesh support grid is circular or semicircular.

29. The apparatus of claim 28, in which the mesh support grid has a diameter of approximately 3 millimeters.

* * * * *